United States Patent [19]

Hogan

[11] Patent Number: 5,800,400
[45] Date of Patent: Sep. 1, 1998

[54] INTRAVASCULAR NEEDLE WITH MOVABLE SAFETY SHIELD

[75] Inventor: John Martin Hogan, Long Beach, Calif.

[73] Assignee: City of Hope, Duarte, Calif.

[21] Appl. No.: 624,491

[22] PCT Filed: Mar. 16, 1995

[86] PCT No.: PCT/US95/02878

§ 371 Date: Apr. 4, 1996

§ 102(e) Date: Apr. 4, 1996

[51] Int. Cl.$^6$ ............................................. A61M 5/32
[52] U.S. Cl. .......................... 604/171; 604/177; 604/263
[58] Field of Search .................................. 604/263, 192, 604/164, 171, 177, 165, 264, 162

[56] References Cited

U.S. PATENT DOCUMENTS

| | | |
|---|---|---|
| 4,676,783 | 6/1987 | Jagger et al. . |
| 4,702,260 | 10/1987 | Wang ................................ 604/264 |
| 4,781,692 | 11/1988 | Jagger et al. . |
| 4,927,415 | 5/1990 | Brodsky ................................ 604/164 |
| 4,935,011 | 6/1990 | Hogan . |
| 4,943,283 | 7/1990 | Hogan . |
| 5,067,945 | 11/1991 | Ryan et al. . |
| 5,085,639 | 2/1992 | Ryan . |
| 5,088,982 | 2/1992 | Ryan . |
| 5,108,376 | 4/1992 | Bonaldo ................................ 604/171 |
| 5,112,311 | 5/1992 | Utterberg et al. ...................... 604/177 |
| 5,112,312 | 5/1992 | Luther . |
| 5,137,515 | 8/1992 | Hogan . |
| 5,154,699 | 10/1992 | Ryan . |
| 5,169,391 | 12/1992 | Vogel . |
| 5,219,339 | 6/1993 | Saito ................................... 604/177 X |
| 5,350,368 | 9/1994 | Shields ................................. 604/263 |
| 5,382,240 | 1/1995 | Lam . |
| 5,401,250 | 3/1995 | Shields ................................. 604/263 X |

*Primary Examiner*—John D. Yasko
*Attorney, Agent, or Firm*—Rothwell, Figg, Ernst & Kurz

[57] ABSTRACT

An intravascular needle with a removable safety shield is disclosed. The arrangement is such that there is little or no impediment of the needle tip control required to efficiently start a needle into the vein.

5 Claims, 5 Drawing Sheets

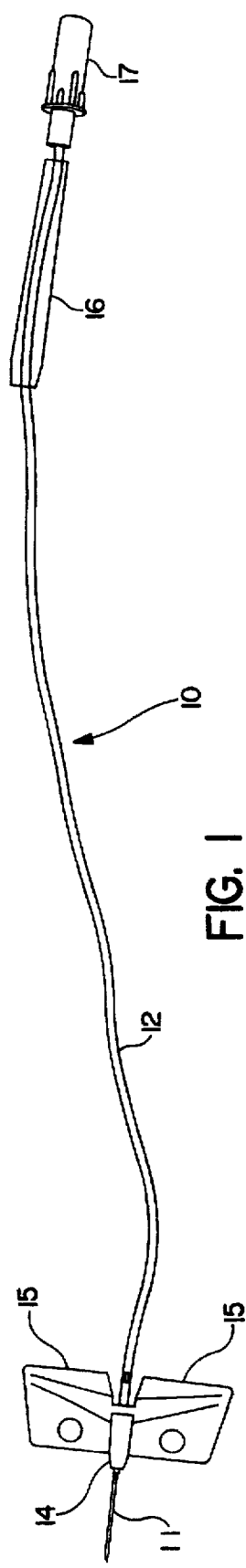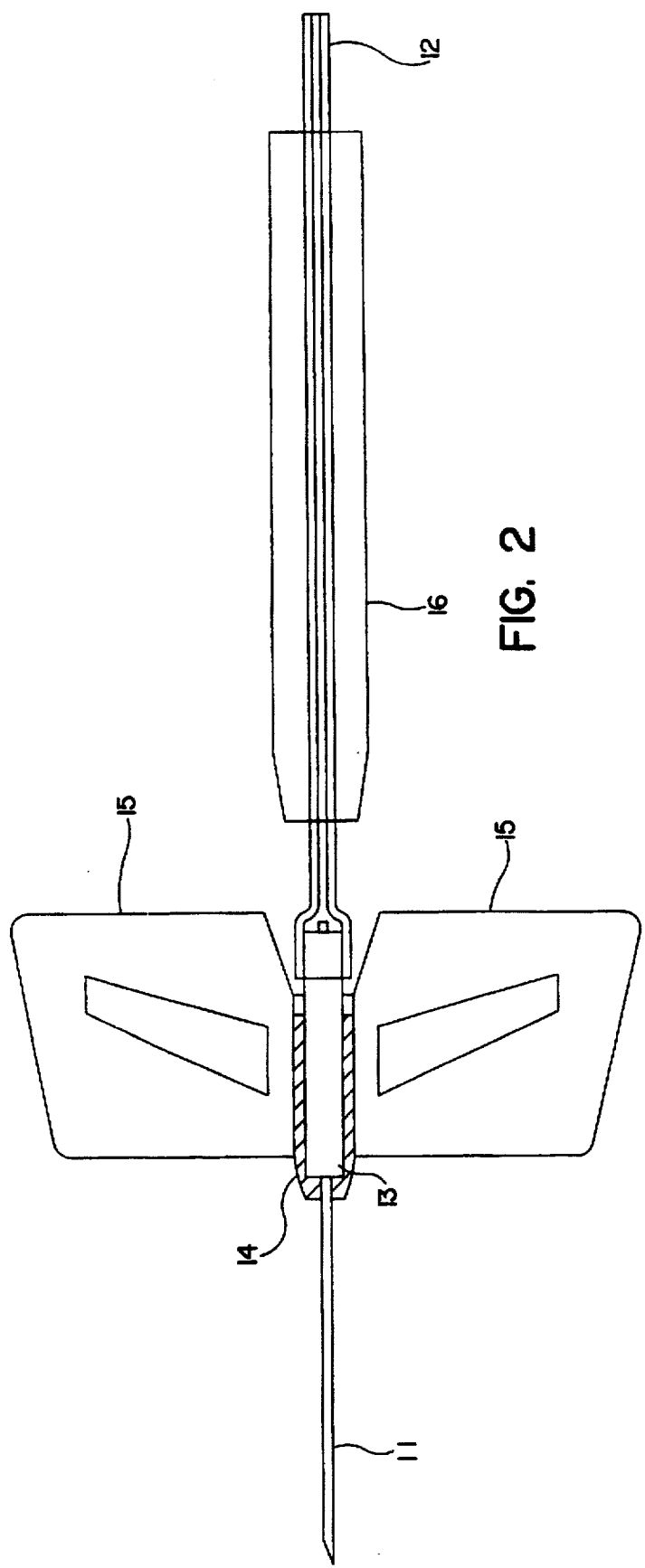

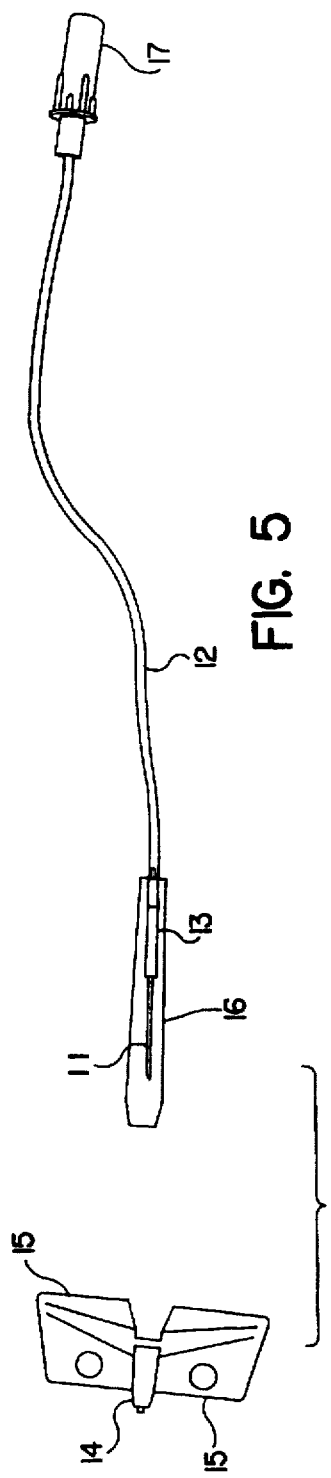
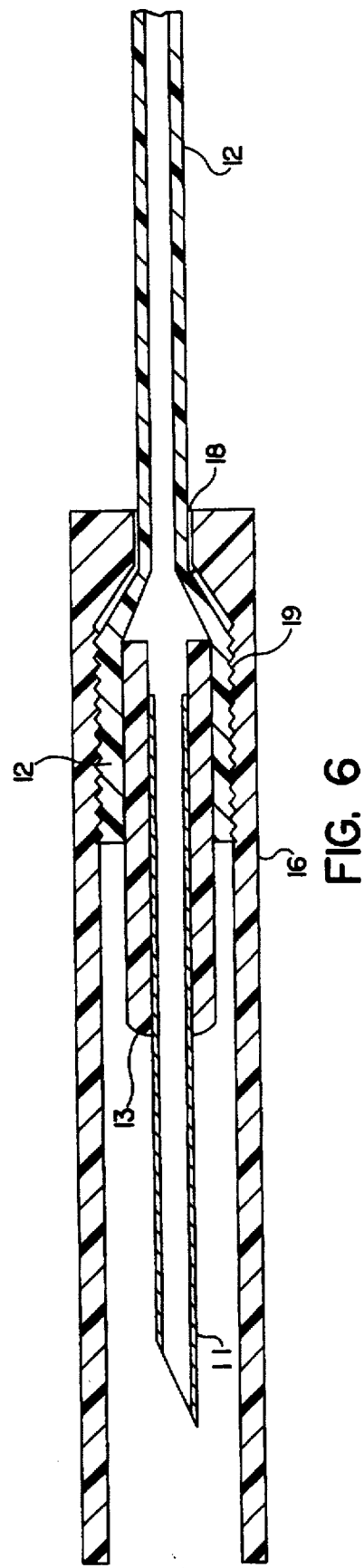
FIG. 5
FIG. 6

INTRAVASCULAR NEEDLE WITH MOVABLE SAFETY SHIELD

TECHNICAL FIELD

This invention pertains to winged needles for the administration of fluids to and the withdrawal of blood samples from patients.

BACKGROUND OF THE INVENTION

Winged needles (also known as butterfly needles) have long been a popular and simple means of gaining intravascular access for administering fluids and medicines to patients. Winged needles are also used for drawing blood samples or performing hemodialysis. The winged finger grips employed in their design offers maximum sensitivity which is important for successful venipuncture. In the relaxed (wings down) position, the wings also provide means for fixing the needle securely, close to the skin puncture site where it cannot be readily jarred.

Known safety shields (see U.S. Pat. Nos. 4,676,783 (Jagger), 4,781,692 (Jagger), 4,935,011 (Hogan), 4,943,283 (Hogan) and 5,137,515 (Hogan) and the Saf-T E-Z set available from Becton Dickinson Co., add considerable bulk to the basic butterfly needle design. For example Hogan patents 4,935,011 and 4,943,283 describe shields which are slidable along a length of tubing and sized to receive a needle and associated gripping means. The bulk added by such shields significantly interferes with the best features of the butterfly needle. It impedes the delicate needle tip control required while starting the needle into a vein. It also extends behind the puncture site, thus increasing the risk of needle dislodgement even by a slight bump.

The use of winged needles is still significant (albeit declining, due to the availability of thin walled catheters) especially for intravascular procedures which do not require long dwell times. Winged needles are often preferred, for example, for giving single bolus injections of medicines and diagnostic agents.

In many countries, price precludes use of intravascular catheters. Butterfly needles cost only $0.25 to $0.50, whereas intravascular catheters may cost $1.75 to $3.00. This price differential gains universal particular importance in this era of cost controls.

The present invention preserves the central features of butterfly needles while also providing a simple and effective safety needle shield slidable along a length of tubing to prevent accidental needle stick injuries.

SUMMARY OF THE INVENTION

This invention provides a safety shield slidable along a length of tubing which is initially in a retracted position away from the needle and associated winged needle gripping means where it does not interfere with the delicate control of the needle tip during venipuncture. In one embodiment of the invention the shield may be used to detach the gripping means from the needle as the needle is withdrawn into the shield.

During venipuncture the wings of the device of this invention are folded upward to pinch and compress the needle so that it is held securely while pushed through the skin and vessel wall. The wings are then allowed to return to a relaxed, flat position. It is a feature of this invention that, in the relaxed position, there is still sufficient friction provided by the wings to prevent passive motion of the needle or of the coupling of the needle to the tubing within the winged gripping means.

A winged needle gripping means is found in the Becton Dickinson Angioset, Intima, and Saf-T Intima catheters as well as the Menlo Care Landmark catheter. However, in these devices the gripping means is not in direct contact with the needle. Instead, the needle is within a catheter which in turn is in contact with the gripping means such that the needle elements cannot be withdrawn from the gripping means by pulling on the connection tubing. The device of this invention permits the needle to be passed back through the winged gripping means by pulling on the connection tubing.

In Jagger, patent 4,676,783, the needle is retracted into a shield by pulling on a special section of tubing. However, the forward end of the shield is prevented from moving backward beyond the base of the needle. The shield adds bulk to the needle end and cannot be retracted along the connection tubing away from the needle. The present invention is therefore an improvement over Jagger.

An important novel feature of this invention is that the movable needle shield can be slid from the initial retracted position along the tubing to a position immediately behind the winged gripping means. Here the needle shield is maintained in a steady position while the connection tube is pulled backward, thus overcoming the friction grip around the needle allowing the needle tip to be retracted from the blood vessel back through the winged gripping means and into the needle shield where it is fixed into position. This may be accomplished while the winged gripping means is still secured to the skin. This is an advantage since butterfly needles have been accidentally removed from veins while attempting to remove tape dressings.

Another advantage of the present invention is that only the needle shield with the enclosed needle and attached tubing needs to be placed in the sharps container. The winged gripping means may be placed in regular refuse cans. Embodiments of the invention wherein the wings are detached in use facilitate disposal of the used needle through narrow mouthed sharps containers.

BRIEF DESCRIPTION OF THE FIGURES

FIG. 1 depicts one embodiment of the invention. The needle shield is shown in a retracted position on the tubing.

FIG. 2 illustrates the FIG. 1 embodiment of the invention in which the top of the needle gripping means is cut away to depict coupling of the needle to the tubing.

In FIG. 3, the needle shield has been advanced along the tubing to a forward position adjacent the back of a winged needle gripping means.

In FIG. 4, the needle is shown retracted into the needle shield.

FIG. 5 depicts the winged gripping means separated from the remainder of the device. The needle base is shown secured in the back of the shield.

FIG. 6 is a longitudinal section of a portion of the device of FIG. 4 or 5, including the retracted needle in the needle shield.

DETAILED DESCRIPTION OF THE INVENTION

The invention is first described by reference to the embodiment of the invention illustrated by FIGS. 1 to 7.

Figure 4:
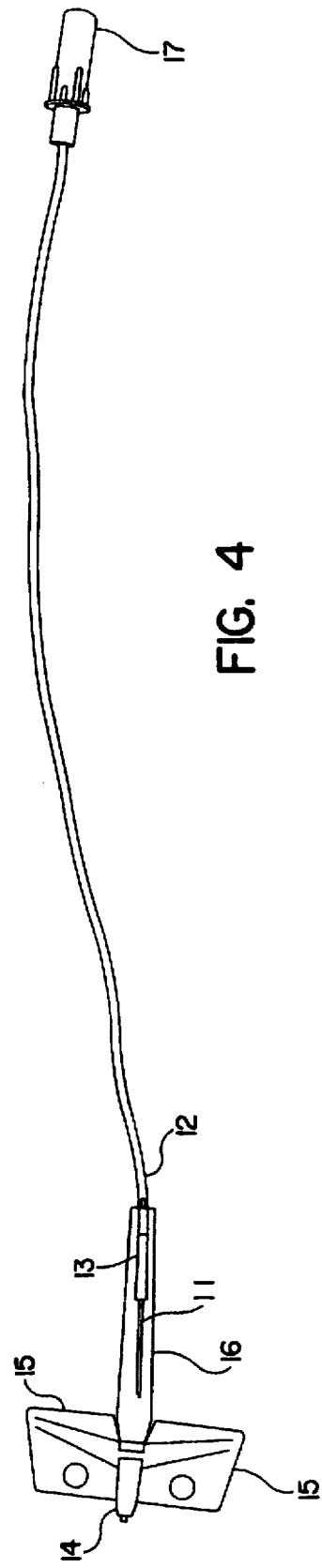
FIG. 4 depicts the same embodiment of the invention as that shown by FIGS. 1 and 3.
Figure 7:
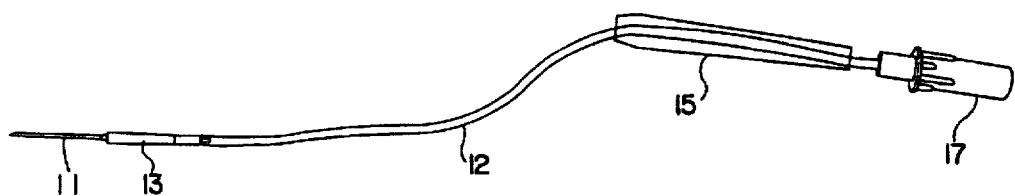
FIG. 7 depicts the needle base embedded in a plastic needle coupling to which tubing is attached. The shield is shown in a position retracted from the needle coupling.

As shown by these figures, the device 10 of the invention comprises an intravascular needle 11 joined to a length of tube 12 through which blood or other fluids may pass. As best shown by FIGS. 2, 4 and 6, the needle 11 is preferably embedded in a plastic needle coupling 13 to which the tube 12 is attached.

The needle 11 is initially exposed in a forward position on the tube 12 in front of the needle gripping means 14 having wings 15. The needle gripping means 14 maintains the needle 11 in this initial position by friction fit.

A cylindrical needle shield 16 slidable along tube 12 is shown in various positions along the tube in FIGS. 1 to 7.

The distal end of the tube 12 may optionally be joined to an injection port and intravenous coupling device 17.

FIG. 4 shows the needle 11 and the needle coupling 13 drawn into the needle shield 16, for example, by pulling on the tube 12 while the shield 16 has been maintained in stationary position, thus overcoming the friction fit of the winged needle grip 14 around the plastic needle coupling 13 and permitting the needle 11 and the needle coupling 13 to slip backward through the winged needle grip 14 into the needle shield 16 in which it is secured. Thereafter, as shown by FIG. 5, the shield 16 containing the secured needle and needle coupling is separated, along with the tube 12 and the injection port 17 from the winged needle grip 14 which may, if desired, remain taped to the skin.

Referring to FIG. 6, the shield 16 containing a retracted needle 11 is shown in section. The back of the shield 16 is provided with an opening 18 sized to permit tube 12 to slide therethrough but to preclude passage of the plastic needle coupling 13 and the associated needle 11. As shown by FIG. 6, the distal end of the shield 16 is provided with internal threads 19 to engage and compress the tubing 12 which is stretched around the distal end of the plastic needle coupling 13. Engagement of the threads 19 compresses the tube 12 against the coupling 13 and secures the needle coupling 13 and the needle 11 in the shield 16.

Referring to the embodiment of the invention shown in FIGS. 1 to 7, during venipuncture, the wings 15 are folded upward to pinch and compress the coupling 13 surrounding the needle 11 within the winged gripping means 14 such that the needle 11 is held securely for passage through the skin and vessel walls.

The wings 15 are then returned or allowed to return to a relaxed flat position usually on the skin surface. The internal surfaces of the needle gripping means 14 provide friction adequate to prevent passive motion of the needle 11 and the needle coupling within the gripping means.

Figure 3:
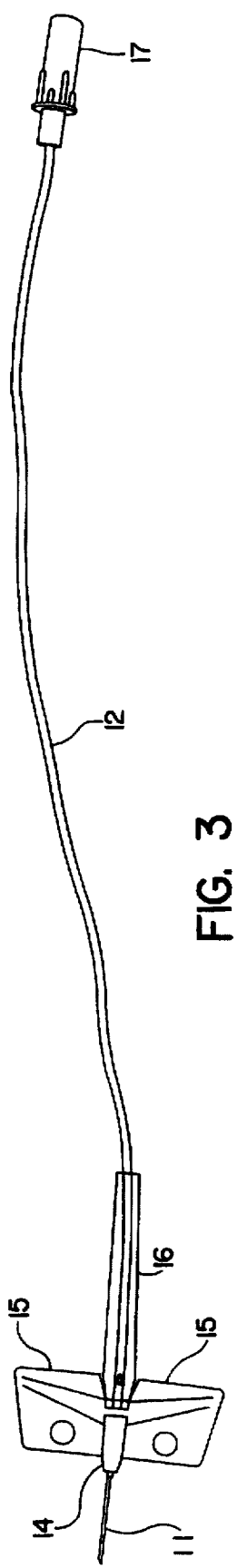
FIG. 3 depicts the same embodiment of the invention as FIG. 1.

To remove the needle 11, the needle shield 16 is slid along the tube 12 from the retracted position shown by FIG. 1 to the advanced or forward position shown by FIG. 3. The needle 11 is then withdrawn into the shield 16 by pulling the tube 12 rearwardly. In this procedure, the needle shield 16 is maintained in a steady position while the tube 12 is pulled backward, thus overcoming the friction grip around the plastic needle coupling 13 allowing the needle tip to be retracted from the blood vessel back through the winged gripping means and into the needle shield 16 where it is fixed into position.

Many possible locking means could be employed to fix the needle 11 and the coupling means 13 within the needle shield. One preferred means is the internal thread 19 at the back of the shield 16 as shown in FIG. 6. The threaded gripping means 19 reliably holds the needle 11 and the needle coupling 13 within the needle shield 16 and offers the manufacturing advantage of allowing the shield to simply be made in an injection mold. The threaded locking means 18 is believed to be novel in this setting.

This may be accomplished while the winged gripping means is still secured to the skin. The risk of accidental removal of the needle from the vein while attempting to remove tape dressings is thus reduced as compared with prior art winged needles.

Figure 8:
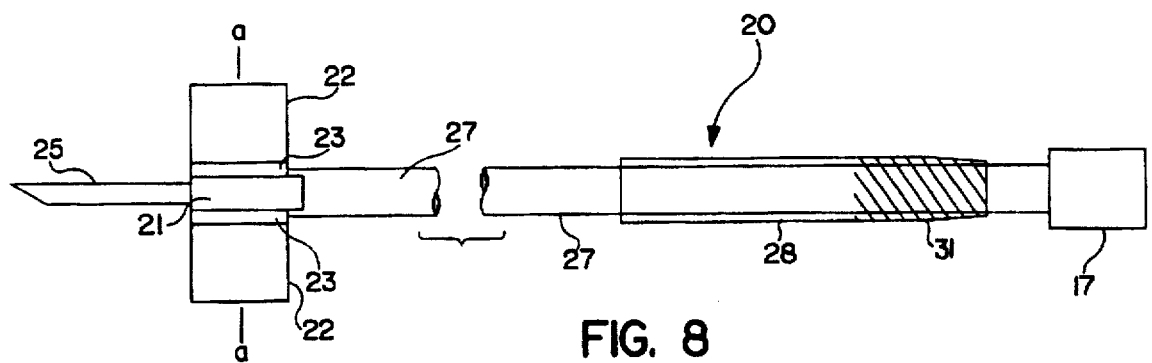
FIG. 8 illustrates another embodiment of the invention in which a winged needle coupling means is permanently fixed to the needle and couples the needle to the tube, whereas in the embodiment of the invention depicted by FIGS. 1 to 7, the winged needle gripping means may be separated from the remainder of the device. In the FIG. 8 embodiment, the wings may be sheared by the needle shield.
Figure 9:
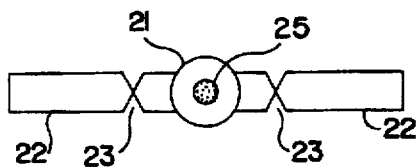
FIG. 9 is a cross-sectional view of the FIG. 8 embodiment taken on the line "a—a".
Figure 11:
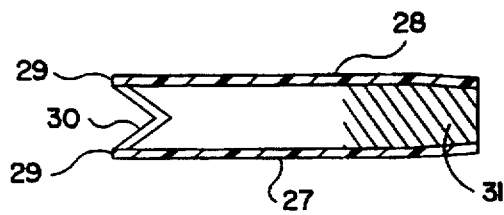
FIG. 11 illustrates a section of a portion of the needle shield of FIG. 8 including a recessed means for shearing the needle wings.
Figure 10:
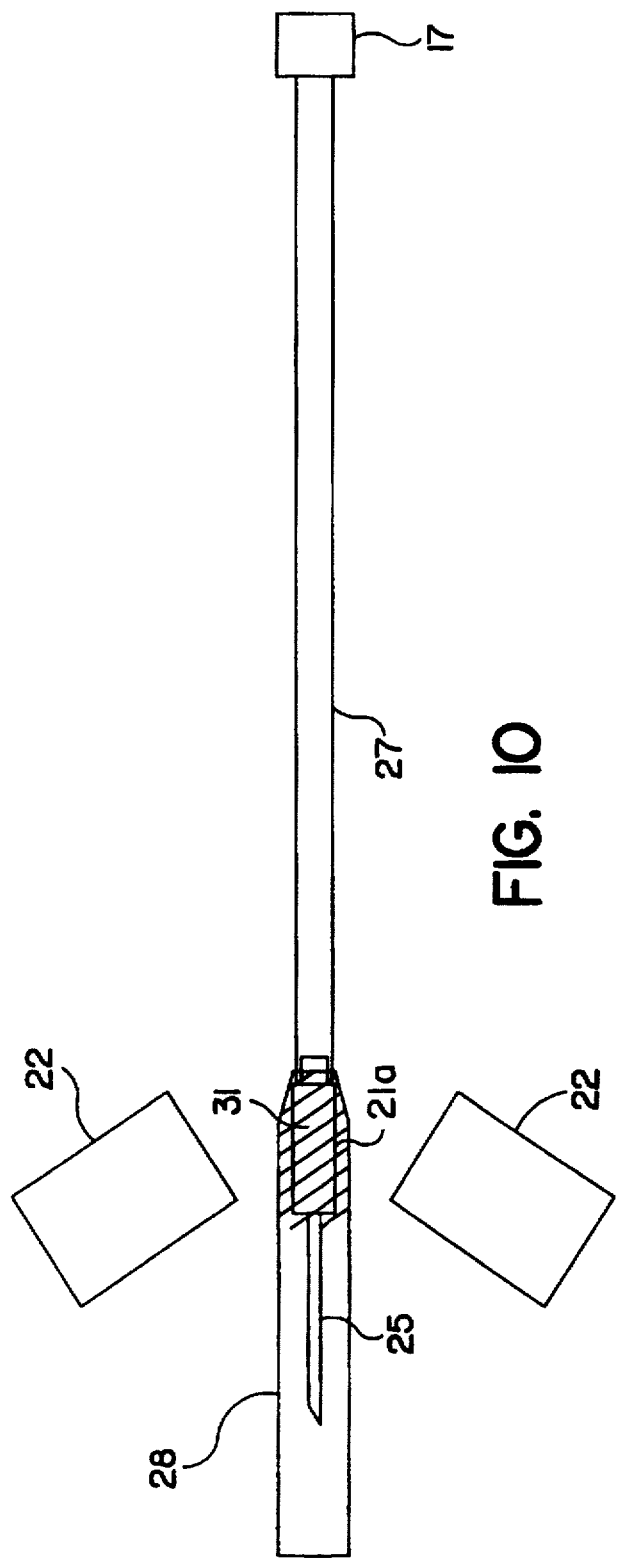
FIG. 10 illustrates the FIG. 8 device with the needle shield in a forward position containing the needle and needle coupling secured therein by internal threads. The wings are shown as sheared by the forward movement of the shield.

In the FIG. 8 embodiment 20 of the invention, a winged needle coupling means 21 having wings 22 is fixed permanently to a needle 25 which secures the needle 25 to tubing 27. Shear lines 23 are provided at the joinder of the wings 22 to the coupling means 21.

Referring to the embodiment 20 of the invention illustrated by FIGS. 8 to 11, the winged needle coupling means 21 has wings 22 joined by shear lines 23. The needle coupling means is permanently fixed to the needle 25. In use, the wings 22 are sheared off by the slidable needle shield 28 which is provided at its proximate or forward end with a blunt or dull leading edge 29 and a recessed shearing means 30. In use, when the needle shield 28 is slid along the tube 27 to a forward position in which it contains the needle 25 and needle coupling 21, the shearing means 30 of the shield 28 shears the wings 22 at the shear lines 23. The needle 25 and sheared needle coupling 21a may be secured in shield 28 by thread means 31. See FIGS. 8, 9 and 10.

I claim:
1. An intravascular needle device comprising:
 (i) a length of tubing through which fluid may pass, said length of tubing having a first end and a second end;
 (ii) said first end of said length of tubing having a needle attachment means provided with a needle;
 (iii) a cylindrical needle shields said needle shield having a lumen surrounding a portion of said length of tubing, said needle shield being slidable along said length of tubing from a position spaced apart from said needle attachment means to a position adjacent said needle attachment means;
 (iv) said lumen of said needle shield being sized to accommodate said needle attachment means, wherein said needle attachment means and said needle are movable into said lumen of said needle shield by pulling said length of tubing in a direction away from said needle attachment means for said needle;
 (v) gripping means for said needle attachment means, said gripping means having passage means therethrough for said needle attachment means; said passage means including friction means to restrain passage of said needle attachment means therethrough; and

(vi) wings on opposite sides of said gripping means for said needle attachment means.

2. The intravascular needle device of claim 1 further comprising:

(vii) means for securing said needle attachment means within said lumen of said needle shield.

3. The intravascular needle device of claim 1 further comprising:

(viii) thread means for securing said needle attachment means within said needle shield after said needle attachment means is moved into the lumen of said needle shield by pulling said length of tubing.

4. The intravascular needle of claim 1 wherein said length of tubing and said cylindrical needle shield having said needle secured therein is separable from said needle gripping means.

5. An intravascular needle device comprising:

(i) a length of tubing through which fluid may pass, said length of tubing having a first end and a second end;

(ii) said first end of said length of tubing having a needle attachment means provided with a needle;

(iii) a cylindrical needle shield, said needle shield having a lumen surrounding a portion of said length of tubing, said needle shield being slidable along said length of tubing from a position spaced apart from said needle attachment means to a position adjacent said needle attachment means;

(iv) said lumen of said needle shield being sized to accommodate said needle attachment means, wherein said needle attachment means and said needle are movable into said lumen of said needle shield by pulling said length of tubing in a direction away from said needle attachment means for said needle; and (v) thread means for securing said needle attachment means within said needle shield after said needle attachment means is moved into the lumen of said needle shield by pulling said length of tubing.

* * * * *